US005789209A

United States Patent [19]
Leathers et al.

[11] Patent Number: 5,789,209
[45] Date of Patent: Aug. 4, 1998

[54] RAPID SCREENING METHOD TO SELECT MICROORGANISM STRAINS THAT PRODUCE A HIGH PROPORTION OF ALTERNAN TO DEXTRAN

[75] Inventors: Timothy D. Leathers; G. Thomas Hayman, both of Peoria; Gregory L. Cote, Edwards, all of Ill.

[73] Assignee: The United States of America as represented by the Secretary of Agriculture, Washington, D.C.

[21] Appl. No.: 641,082

[22] Filed: Apr. 29, 1996

Related U.S. Application Data

[63] Continuation of Ser. No. 284,312, Aug. 2, 1994, abandoned.
[51] Int. Cl.$^6$ ..................................................... C12P 19/04
[52] U.S. Cl. ........................... 435/101; 435/103; 435/34; 435/172.1
[58] Field of Search ................................ 435/101, 103, 435/34, 172.1

[56] References Cited

PUBLICATIONS

Cote, G. L., "Low–viscosity α–D–glucan fractions derived from sucrose which are resistant to enzymatic digestion," *Carbohydrate Polymers* 19:249–252 (1992).
Cote, G. L. and Robyt, J. F., "Isolation and Partial Characterization of an Extracellular Glucansucrase from *Leuconostoc mesenteroides* NRRL B–1355 that Synthesizes an Alternating (1→6), (1→3)–α–D–Glucan," *Carbohydrate Research* 101:57–74 (1982).
Jeanes, A. et al., "Characterization and Classification of Dextrans from Ninety–six Strains of Bacteria," *Journal of the American Chemical Society* 76:5041–5052 (1954).
Lawford, G.R., Kligerman, A., and Williams, T., "Dextran Biosynthesis and Dextransucrase Production by Continuous Culture of *Leuconostoc mesenteroides*," *Biotechnology and Bioengineering* 21:1121–1131 (1979).
Jeanes, A., "Preparation of Dextrans from Growing Leuconostoc Cultures," *Methods in Carbohydrate Chemistry* 5:119–132 (1965).
Smith M., (approved Jan. 14, 1994) Tektran database summary: "Polysaccharide Mutants of *Leuconostoc Mesenteroides* NRRL B–1355".
Smith, M., (approved Feb. 1994) Annual Research Progress Report, available on CRIS file on DIALOG.
Smith, M. and Zahnley, J., "*Leuconostoc mesenteroides* NRRL B–1355 Viscosity Mutants," (Abstract O–77) American Society for Microbiology Annual Meeting, May 27 (1994). (first publicly available about Mar. or Apr. 1994).
Smith, M. R., Zahnley, J., and Goodman, N., "Glucosyltransferase Mutants of *Leuconostoc mesenteroides* NRRL B–1355," *Applied and Environmental Microbiology* 60:2723–2731 (Aug. 1994). (published Jul. 27, 1994).
Robyt, J. F., "Selection of Mutants of *Leuconostoc mesenteroides* Constitutive for Glucansucrases," (Abstract) American Society for Microbiology, 53rd Annual Meeting, Ames, Iowa, Oct. 28–30 (1993).
Kim, D. et al., "Properties of *Leuconostoc mesenteroides* Constitutive Dextransucrases," (Abstract O–72) American Society for Microbiology Annual Meeting, May 27 (1994). (first publicly available about Mar. or Apr., 1994).
Kim, D. and Robyt, J. F., "Production and selection of mutants of *Leuconostoc mesenteroides* constitutive for glucansucrases," *Enzyme Microb. Technol.* 16:659–664 (Aug. 1994).
Crueger et al "Biotechnology", pp. 9–29, 1990.
Cote et al., *Carbohydr. Res.*, vol. 101, 1982, pp. 57–74.
Harada et al., In "Extracellular Microbial Polysaccharides", 1977 PA. Sanford ed., pp. 265–269, 1977.
Lopez–Munguia et al., Enzyme Microb. Technol., vol. 15, 1993, pp. 77–85.
Summer et al, J. Biol. Chem., vol. 108, pp. 51–54, 1935.
Robyt, J., "Dev. Carbohydrate Chem.", pp. 261–292, 1992.

*Primary Examiner*—Irene Marx
*Attorney, Agent, or Firm*—Nancy J. Parsons; Margaret A. Connor; M. Howard Silverstein

[57] ABSTRACT

A rapid screening procedure to select microorganism strains that produce a high proportion of alternan to dextan and a high proportion of alternansucrase to dextransucrase is described. Strains selected by the method are useful to produce a high proportion of alternansucrase to dextransucrase and to produce a high proportion of alternan to dextran, either fermentatively by cultivation of the strains on sucrose, or enzymatically by using alternansucrase produced by the strains of the invention. The selected strains can also be used to obtain microorganism strains having further improvements.

3 Claims, 3 Drawing Sheets

ALTERNAN

DEXTRAN

SCREENING PROCEDURE

RAPID SCREENING METHOD TO SELECT MICROORGANISM STRAINS THAT PRODUCE A HIGH PROPORTION OF ALTERNAN TO DEXTRAN

This application is a continuation, of application Ser. No. 08/284,312, filed Aug. 2, 1994 now abandoned.

BACKGROUND OF THE INVENTION

1. Field of the Invention

The present invention relates to novel microorganism strains that produce a high proportion of alternan to dextran and a rapid screening procedure to select these strains. Strains selected by the method are useful to produce a high proportion of alternansucrase to dextransucrase and to produce a high proportion of alternan to dextran, either fermentatively by cultivation of the strains on sucrose, or enzymatically by using alternansucrase produced by the strains. The selected strains can also be used to obtain microorganism strains having further improvements.

2. Description of the Related Art

Alternan is the name given to the unique α-D-glucan soluble glucose-polysaccharide in which alternating α-(1→6), α-(1→3) linkages predominate in the polysaccharide backbone (see FIG. 1). Alternan and low-molecular weight derivatives of alternan have unique properties that resemble certain functional characteristics of gum arabic, maltodextrins or Polydextrose™ (G. L. Cote, *Carbohydrate Polymers* 19:249–252 (1992)). Alternan has potential commercial applications as a low-viscosity bulking agent and extender in foods and cosmetics. Alternan is resistant to hydrolysis by known endoglucanases and is a poor substrate for most exoglucanases (Cote, supra). Thus, alternan and alternan derivatives have potential value as noncaloric, carbohydrate-based soluble food additives in artificially sweetened foods. In addition, the valuable sweetener fructose is a by-product of the enzymatic synthesis of alternan.

Certain naturally occurring strains of *Leuconostoc mesenteroides*, such as strains NRRL B-1355, NRRL B-1498, and NRRL B-1501, have been found that synthesize some alternan extracellularly, from sucrose. The bacteria secrete a glucosyltransferase called alternansucrase, that transfers glucose to the growing polymer chain and releases fructose for use as a carbon source. However, all of these isolates also produce significant amounts of the polysaccharide dextran (a polysaccharide containing a backbone of D-glucose units linked predominantly α-D(1→6)) (see FIG. 2). Dextrans possess higher viscosity, lower solubility, and are more susceptible to enzymatic digestion than alternan, thus it is desirable to obtain alternan with a minimum of dextran.

Presently, no way exists to readily select microorganism strains that produce a high proportion of alternan to dextran. While dextrans are made by many microorganisms strains, alternan is rare, made by only a few such as those noted above. No naturally-occurring strains are known that produce a high proportion of alternan to dextran. The fact that alternan is produced in conjunction with significant amounts of dextran means that a significant amount of the sucrose utilized by the bacteria is converted into unwanted dextran. The alternan must then be separated by costly procedures, such as enzyme digestion and dialysis, ethanol fractional precipitation, or other methods. It has been reported that strain NRRL B-1355 produces roughly equal quantities of dextran and alternan (A. Jeanes et al., *Journal of the American Chemical Society* 76:5041–5052 (1954)). In order to obtain alternan with a small proportion of dextran, for example, fermentatively using strain NRRL B-1355, it must be physically separated from the culture supernatant which contains approximately 50% dextran. There is a slight and narrow differential solubility of alternan and dextran in aqueous ethanol solutions (G. L. Cote and J. F. Robyt, *Carbohydrate Research* 101: 57–74 (1982)). While alternan can be differentially precipitated, the separation procedure is difficult and costly. Further, as discussed above, another disadvantage of production of 50:50 alternan:dextran is that approximately half of the sucrose utilized by the bacteria is converted into unwanted dextran.

Alternan can also be obtained enzymatically, by synthesis from sucrose using the enzyme, alternansucrase. This enzyme is known to be produced by the naturally-occurring microorganism strains noted above that produce alternan. However, these strains produce alternansucrase in conjunction with the production of significant amounts of dextransucrase, an enzyme which synthesizes dextran from sucrose. Alternansucrase must then be purified from dextransucrase. This has been reported, but purification is difficult, and enzyme yields are low (Cote and Robyt, supra).

What are needed are microorganism strains that produce a high proportion of alternan to dextran and that produce a high proportion of alternansucrase to dextransucrase.

SUMMARY OF THE INVENTION

We have discovered a screening procedure to rapidly and easily screen hundreds of microorganisms to select those strains that produce a high proportion of alternan to dextran and produce a high proportion of alternansucrase to dextransucrase. By use of this screen, novel microorganism strains having these properties are selected. The invention also encasses use of the selected strains to produce a high proportion of alternansucrase to dextransucrase and to produce a high proportion of alternan to dextran, either fermentatively by cultivation of the strains on sucrose, or enzymatically by using alternansucrase produced by the strains of the invention. The selected strains can also be used to obtain microorganism strains having further improvements.

In accordance with this discovery, it is an object of the invention to provide a rapid screening method to identify microorganism strains that produce a high proportion of alternan to dextran and produce a high proportion of alternansucrase to dextransucrase. In brief, in our screening method, test strains are grown in a sucrose-containing nutrient medium; dextranase is added and the samples are incubated to hydrolyze any dextran present in the polysaccharide produced by the test strains. Each test culture is treated with a reagent, e.g., dinitrosalicylic acid, that produces color in the presence of reducing sugar, and the reducing sugar content is measured. Positive and negative controls are included. Test strains that produce a high proportion of alternan to dextran are only slightly darker by eye than the negative controls. These strains exhibit an optical density (OD) reading at 540 nm of no greater than about 0.3 OD unit higher than negative controls and show about 1–2 mg/ml reducing sugar equivalents greater than negative controls (based on a maltose standard curve).

Our method is useful to screen naturally-occurring strains, purified isolates and mutants obtained from naturally-occurring strains or purified isolates. The method is especially useful for screening mutants, particularly those generated from known dextran-alternan-producing strains.

It is also an object of the invention to provide microorganism strains that produce a high proportion of alternan to dextran and that produce a high proportion of alternansucrase to dextransucrase.

A further object of the invention is the production of a high proportion of alternan to dextran, by microbial fermentation using the strains of the invention or by enzymatic synthesis using alternansucrase produced by strains of the invention.

Another important object of the invention is use of the strains to produce a high proportion of alternansucrase to dextransucrase using the microorganism strains of the invention.

The selected strains can also be used to obtain microorganism strains having further improvements.

Other objects and advantages of the invention will become readily apparent from the ensuing description.

DETAILED DESCRIPTION OF THE INVENTION

Screening Method

Figure 1:
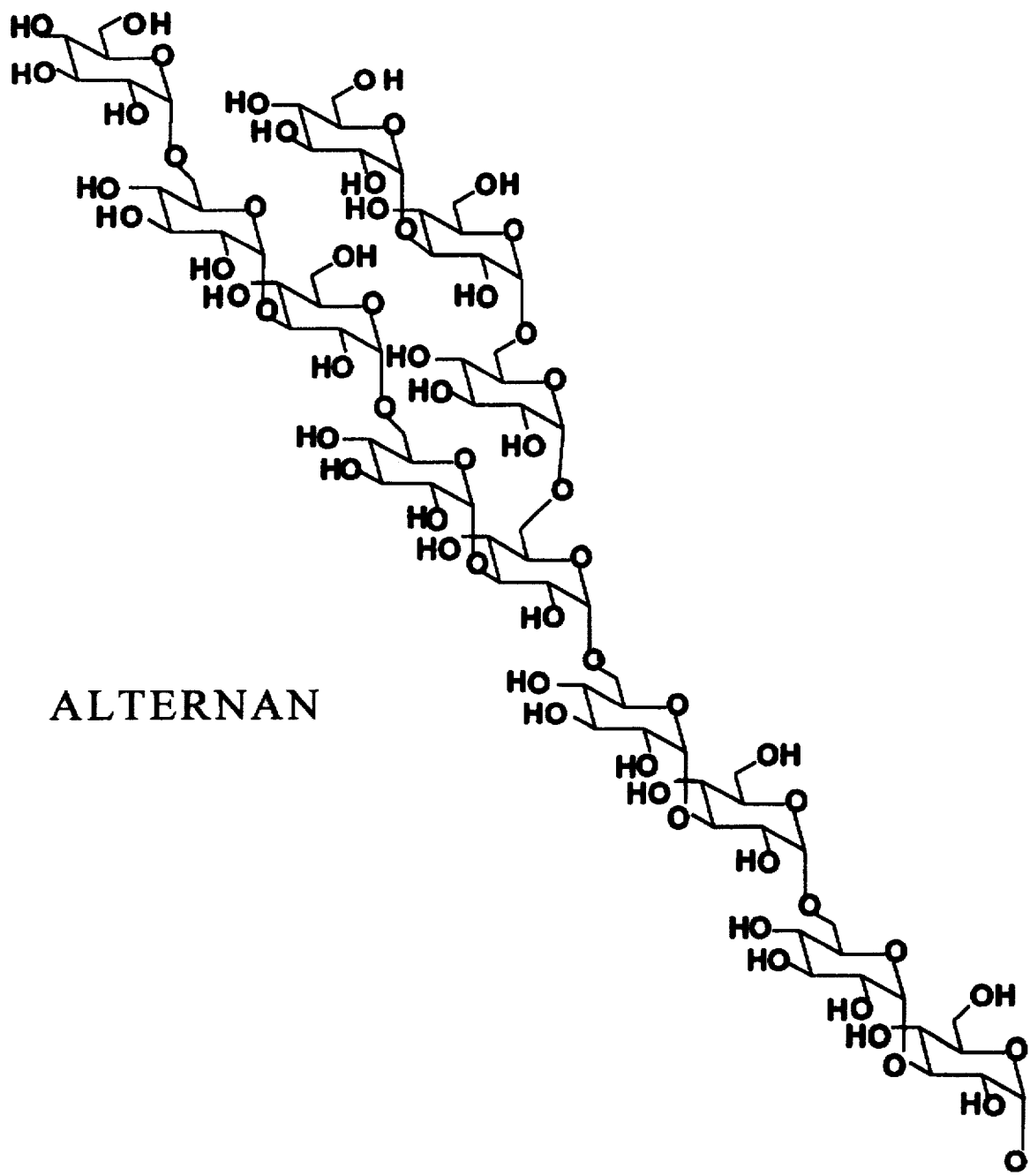
FIG. 1 illustrates the structure of alternan.
Figure 2:
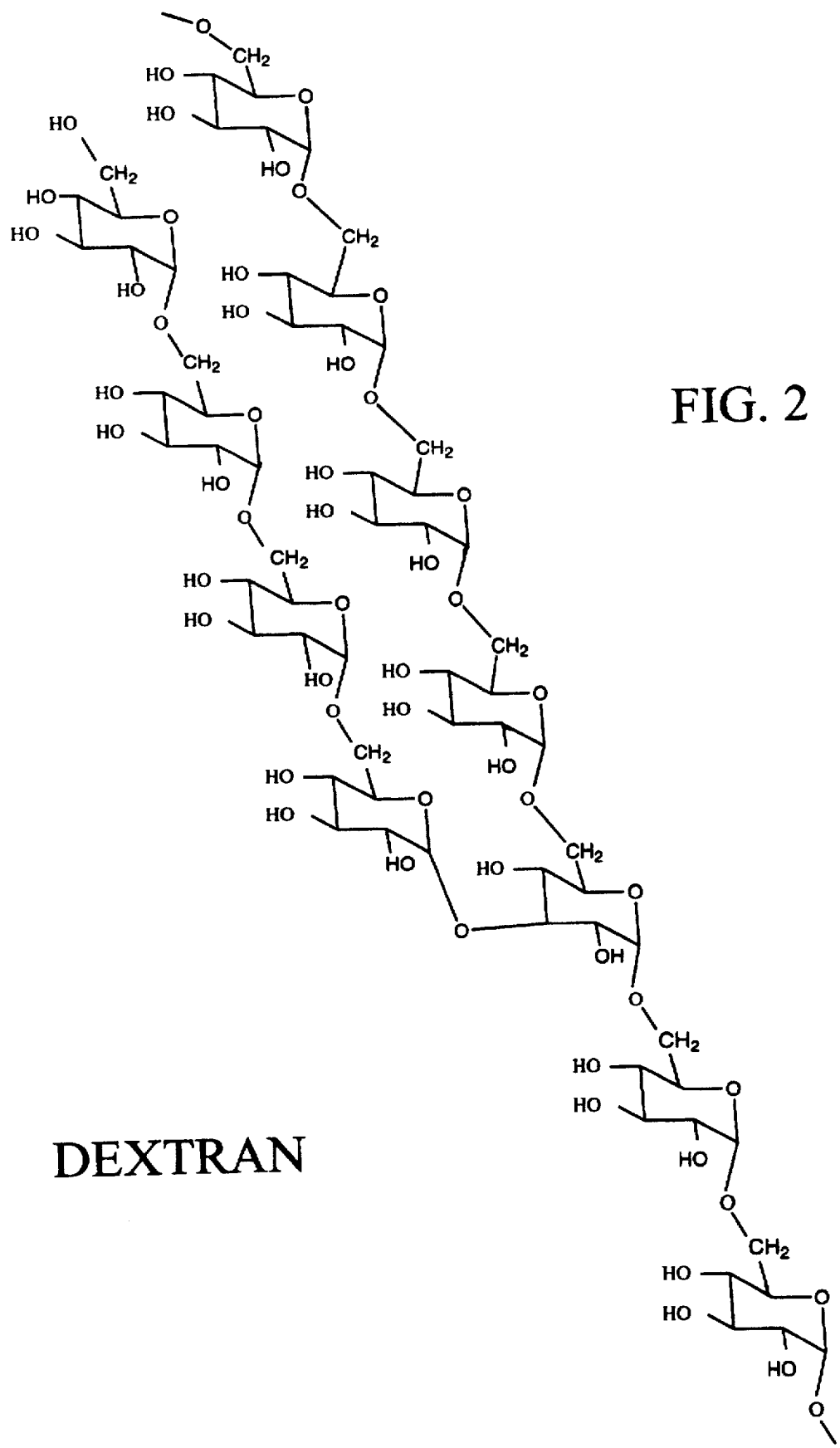
FIG. 2 illustrates the structure of dextran produced by L. mesenteroides strain NRRL B-512F. This dextra contains 95% α-(1→6) linked glucose and 5% α-(1→3) branch linkages. It is used for commercial production of dextran in North America and Europe.

In the screening method of the invention, hundreds of organisms can be rapidly screened to select those which produce a high proportion of alternan to dextran and which produce a high proportion of alternansucrase to dextransucrase. In brief, in the screening method of the invention, the test isolates are cultured on a sucrose-containing nutrient medium to produce polysaccharide. Dextranase is added and the samples are incubated to hydrolyze dextran and release reducing sugars. Positive and negative controls are inoculated and incubated along with the test samples. The positive control comprises a wild-type strain, e.g., NRRL B-1355, a known alternan and dextran-producing strain, to which dextranase has been added. The negative control comprises the same wild-type strain to which no dextranase has been added. Next, a reagent which produces a colored compound in the presence of reducing sugar, e.g., dinitrosalicylic acid, is added to the test isolates and controls, and the reducing sugar content is assessed visually or measured quantitatively using a spectrophotometer. Test strains that produce a high proportion of alternan to dextran are only slightly darker by eye than the negative controls. These strains exhibit an optical density (OD) reading at 540 nm of no greater than about 0.3 OD unit higher than negative controls and show about 1-2 mg/ml reducing sugar equivalents greater than negative controls (based on a maltose standard curve).

Sources of Microorganism Strains for Screening

The sources of microorganism strains for screening include naturally-occurring strains, purified isolates, and mutants obtained from naturally-occurring strains or purified isolates. The preferred sources of strains for screening or for production of mutants for screening are bacteria known to produce α-D-glucans, especially dextrans. (Jeanes et al., Journal of the American Chemical Society 76: 5041–5052 (1954), describes dextran-producing bacteria.) The more preferred strains are strains of Leuconostoc mesenteroides including subspecies mesenteroides and dextranicum. These are described in Bergey's Manual of Systematic Bacteriology, E. I. Garvie "Genus Leuconostoc," Williams and Wilkens, Baltimore (1986). Specific dextran-producing strains are readily identifiable by assaying for the presence of dextran in the polysaccharide produced by the strain, as described in detail below. Preferred strains are those strains which are known to produce some alternan, for example, NRRL B1498, NRRL B-1501, and NRRL B-1355.

Generation of Mutants

In one embodiment of the invention, mutant strains are generated and screened for the ability to produce a high proportion of alternan to dextran. By way of example, one may obtain suitable mutants for screening by selecting a parent strain having the ability to produce alternan in conjunction with dextran, e.g., NRRL B-1355. Mutant strains are created by subjecting the parent strain to mutation using mutagens known in the art. These include, for example, chemical mutagens such as ICR 191, ethylmethane sulfonate, N-methyl-N'-N-nitrosoquanidine, or physical mutagens, such as ultraviolet (UV) radiation. Mutagenesis procedures and isolation of mutants are known. (See J. H. Miller, Experiments in Molecular Genetics, Cold Spring Harbor Laboratory (1972), pp. 111–185, which is herein incorporated by reference.)

A preferred method for obtaining mutant strains for use in the screening method of the invention involves culturing a parent strain in a liquid medium and subjecting the cells to UV radiation to induce mutation. Any level of mutagenesis can be used. However, as known to those in the art, the higher the mutagenesis that takes place, the higher the percentage of mutants recovered. By way of example, one may expose the cells to 300 to 350 $\mu W/cm^2$ radiation for a period ranging from about 10 to 30 seconds. We have found that samples showing approximately 99% mortality are useful for screening. A period of usually 20 seconds for L. mesenteroides strain NRRL B-1355 has been found to be optimal to obtain a 99% mortality rate. Subsequent to mutation, the resultant strain is grown up and screened as described below to select the specific colony or colonies which produce a high proportion of alternan to dextran.

Rapid Screening Procedure

Figure 3:
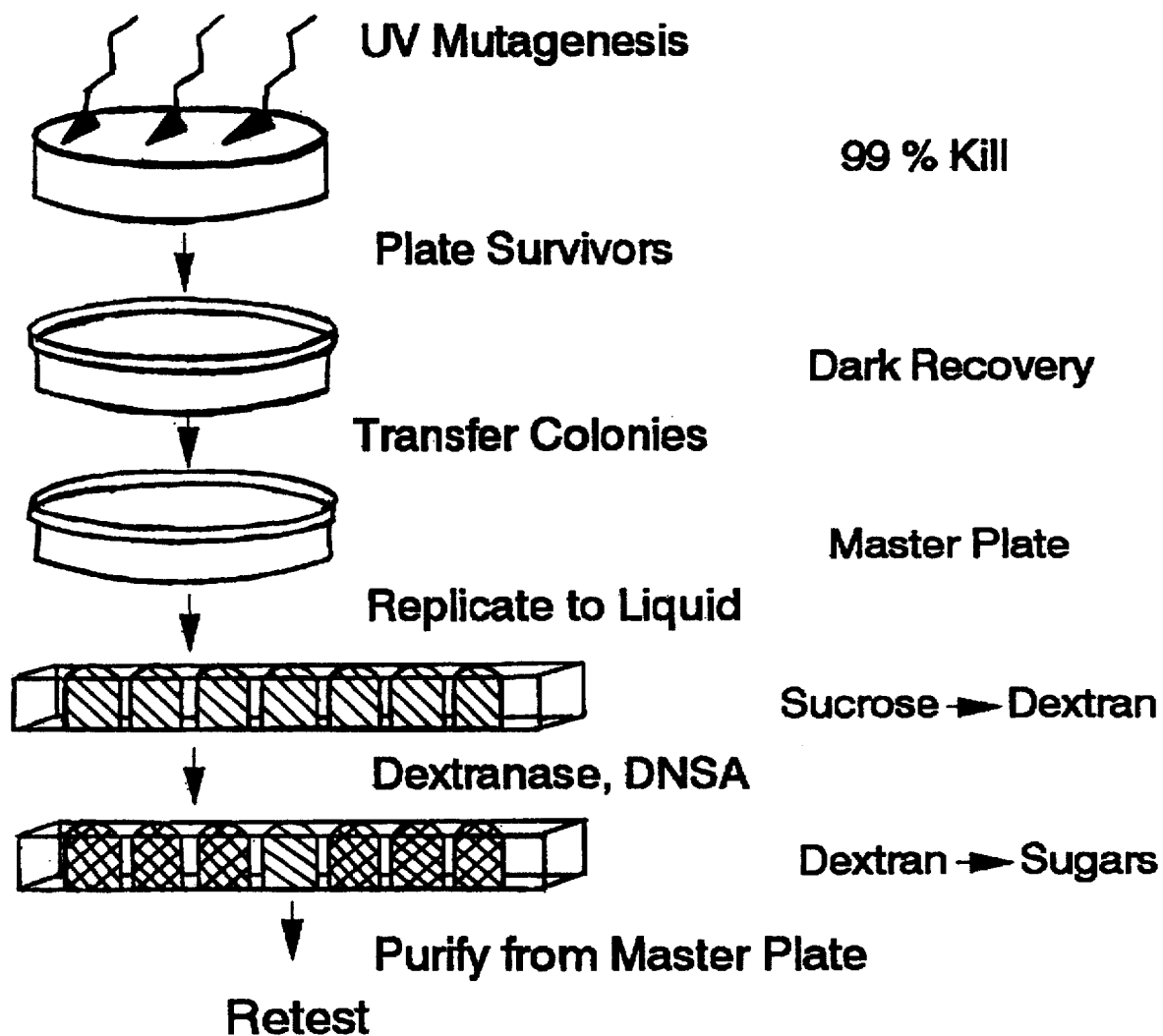
FIG. 3 illustrates the screening of mutant strains by a preferred embodiment of the rapid screening procedure of the invention. The abbreviation DNSA refers to the color reagent, dinitrosalicylic acid.

The naturally-occurring strain, purified isolate or mutant generated as described above, is screened to isolate the specific colony or colonies which produce a high proportion of alternan to dextran. FIG. 3 illustrates a preferred embodiment of the screening procedure of the invention.

The screening is carried out as follows: The test strains are inoculated onto a suitable growth medium. Such a medium includes, for example, an assimilable carbon source, e.g., sucrose, maltose, and assimilable sources of nitrogen and inorganic salts. Such nitrogen and inorganic salts sources can be complex sources of proteins and vitamins such as beef extract, polypeptone, yeast extract, and corn steep liquor. The plates are incubated at a time and temperature to produce isolated colonies. Preferably, the strains are incubated in the dark. For example, L. mesenteroides organisms grow at a broad temperature range, e.g., 10°–37° C.; optimum growth is at 20°–30° C.

Isolated colonies are transferred onto fresh plates (master plates) of a suitable growth medium as described above. It is preferred that the isolated colonies are transferred in a grid pattern. We have found that rapid screening of hundreds of colonies can be readily accomplished by transferring the isolated colonies in a grid pattern corresponding to 96-well microtiter dishes. The colonies are grown at a time and temperature to produce visible growth. The master plates are used to inoculate liquid cultures comprising a sucrose-containing nutrient medium suitable for growth of the colonies. The cultures are grown with or without shaking to produce polysaccharide. We have found that inoculation of liquid cultures in sterile 96-well microtiter dishes (0.1 ml/well), for example, using a replica plater, is convenient.

Next, dextranase (1,6-α-D-glucan-6-glucanohydrolase, EC 3.2.1.11), is added to each well. This enzyme hydrolyzes the α-1→6 glucosidic linkages of the bacterial polysaccharide dextran to yield reducing sugars. The plates are mixed briefly and incubated at a time and temperature sufficient to hydrolyze dextran that may be present in the polysaccharide produced by the test cultures when grown on sucrose. Surprisingly, we have found that "crude" dextranase is preferable over purified dextranase. It is believed that this is because the crude enzyme preparations apparently include enzymes able to convert the nonreducing sugar sucrose into reducing sugars. Thus, the use of crude dextranase eliminates apparent mutants that actually produce low levels of dextran as a consequence of poor growth and substrate utilization.

Positive and negative controls are included on each microtiter plate. The positive controls comprise wells inoculated from colonies of a wild-type strain, e.g., NRRL B-1355, a known alternan and dextran-producing strain, to which dextranase has been added. The negative controls comprise wells inoculated from colonies of the same wild-type strain, however, no dextranase is added. Where the test samples are mutant strains, the positive and negative controls comprise the non-mutagenized, parent microorganism strain used to generate the mutants.

A reagent which produces color in the presence of reducing sugar, e.g., dinitrosalicylic acid, is added to the test isolates and controls. The samples are incubated at a time and temperature to develop the reaction between the color reagent and reducing sugar released by the dextranase. A microassay can be conveniently carried out as follows: 0.1 ml of a solution consisting of 30% sodium potassium tartrate, 1.6% sodium hydroxide, and 1.0% dinitrosalicylic acid is added to the culture in each well. The cultures are mixed briefly, and incubated at 80° C. for 15 to 30 minutes to develop the reducing sugar color reaction.

Clear distinctions between the positive and negative control wells can be readily visually observed. Typically, the positive controls (representing isolates that produce wild-type levels of dextran) appear dark brown in this assay. Negative controls (representing wild-type cultures but to which no dextranase has been added) appear lighter/orange-colored. Putative strains which produce a high proportion of alternan to dextran are only slightly darker by eye than the negative controls.

A convenient way to detect putative strains that produce a high proportion of alternan to dextran is to measure optical density, preferably zeroing the spectrophometer using the negative control, and then reading the optical densities of the positive control and the test samples. As an example, an assay using dinitrosalicylic acid as described above produces positive control wells with optical densities at 540 nm of approximately 1.0 optical density (OD) unit above those of negative control wells. Putative strains that produce a high proportion of alternan to dextran are identified by wells that are only slightly darker than negative controls, that is, at 540 nm, they are no more than about 0.3 OD unit higher than negative controls. Color development can vary among individual plates by 0.3 OD unit or more, thus positive and negative controls are included on each plate for comparison. Strain NRRL B-21138 which was obtained by the screening method of the invention (see Example 1, below) typically exhibited optical densities of approximately from 0.1 to 0.3 OD unit higher than negative controls.

The assay can be carried out by "trained eye" or can be automated.

Quantitative measurement of test samples can also be carried out using a spectrophotometer to measure color intensity at 540–575 nm to determine the reducing sugar equivalents of the test sample and the positive and negative controls. Reducing sugar equivalents are obtained by measuring the optical density and comparing the values to a standard curve prepared using a reducing sugar standard, e.g., maltose. This may be conveniently done by preparing a standard curve using solutions of maltose of known concentration (e.g., 0.1 ml of solutions of purified maltose in a concentration range of 10 mg/ml to 0.4 mg/ml). The maltose solutions are reacted with the color reagent as described above, and the optical density at 540–575 nm is measured.

Negative control wells (containing cells of the parental strain, spent medium components, and polysaccharides, but to which no dextranase was added) exhibit a reducing sugar background equivalent to approximately 2–4 mg/ml of maltose when read against a blank made up of 50 mM sodium acetate pH 5.0 buffer treated with the color reagent as described above. Positive control wells (identical to negative controls, except treated with dextranase) exhibit a reducing sugar response equivalent to approximately 4 mg/ml of maltose greater than negative controls (i.e., 6–8 mg/ml total maltose). Putative strains that produce a high proportion of alternan to dextran show a reducing sugar response equivalent to approximately 1–2 mg/ml maltose greater than negative controls (i.e., 3–5 mg/ml total maltose).

Confirmation of Alternan Purity

Alternan purity can be readily determined in a number of ways, including differential precipitation with alcohol and radioassay. In the differential precipitation method, the alternan product obtained by growth of a strain obtained by the screening assay, is treated with alcohol to precipitate polysaccharide. Alternan precipitates at slightly higher concentrations of ethanol than does dextran. Cote and Robyt, supra, report that an S-fraction (alternan) and an L-fraction (dextran) produced by *L. mesenteroides* NRRL B-1355 when grown on sucrose precipitated at 40% and 38% ethanol, respectively. The amount of each precipitated polysaccharide is then measured, for example, by gravimetric or calorimetric means.

A radioassay to determine alternan purity is described by Cote and Robyt, supra, which is herein incorporated by reference. In this method, the cell-free culture fluid from the microorganism strain is incubated with $^{14}C$-labelled sucrose for a given time. The $^{14}C$-labelled polysaccharide which is formed is precipitated by addition of alcohol such as ethanol, methanol, or isopropyl alcohol. The relative amounts of alternan and dextran can be determined using a hydrolytic enzyme to destroy one polysaccharide, leaving the other intact, and measuring how much labelled polysaccharide remains after hydrolysis. For example, dextranase hydrolyzes dextran so that it is no longer a polysaccharide, and therefore no longer precipitated by alcohol. Alternan purity is determined as the percent of total precipitable counts after exhaustive digestion by dextranase.

In a typical example, radiolabelled sucrose is added to the cell-free culture fluid of the microorganism strain obtained by the screening assay. After a given period, the radioactive polysaccharide formed is precipitated with alcohol (>42% by vol). A solution of the radioactive polysaccharide is then mixed with a solution of dextranase, and the amount of polysaccharide that remains unhydrolyzed after dextranase hydrolyzes dextran present is determined as alternan. Determination of alternan purity by radioassay is described in detail, below, in Example 2.

Confirmation of Alternansucrase Purity

The proportion of alternan to dextran and the proportion of alternansucrase to dextransucrase formed by a strain are related as follows. An alternan-dextran-producing microorganism strain, when grown in the presence of the inducer sucrose, synthesizes the two enzymes, alternansucrase and dextransucrase, that are secreted into the surrounding medium. Whenever alternansucrase or dextransucrase are present in active form, sucrose will be converted into alternan or dextran, respectively. Therefore, in cultures of an alternan-dextran producing strain that are grown in sucrose-containing media, both the enzymes and the polysaccharides will be present. The bacteria make the enzymes, and the enzymes convert sucrose into polysaccharide. Thus, the proportion of alternan to dextran and the proportion of alternansucrase to dextransucrase are the same. Stated another way, the percent alternan the total polysaccharide is the same as the percent alternansucrase of total sucrase.

The amount of either enzyme present in active form in a mixture can be determined by measuring how much of its product polysaccharide is formed from sucrose in a given time period. In order to determine in a mixture of alternansucrase and dextransucrase how much of each enzyme is present, the amount of each polysaccharide formed from sucrose in a given time is measured. In a typical procedure, sucrose is added to an enzyme-containing, and after a given time, the amount of each polysaccharide formed is measured by any one of a number of methods, as described in detail above. For example, in the differential precipitation method, if a mixture produces from sucrose in one day one gram of dextran and one gram of alternan, that indicates that the original mixture contained a 50:50 mixture of dextransucrase and alternansucrase.

Confirmation of the Identity of the Polysaccharide as Alternan

Alternan production may be confirmed by the methylation procedure described by M. E. Slodki et al., *Carbohydrate Research* 156:199-206 (1986) which is herein incorporated by reference, or by physical (especially rheological) properties of the polysaccharide produced.

Where the strains screened by the method are those known to produce alternan, for example, mutants prepared from parent strains known to product alternan and dextran, alternan confirmation is not required.

Genetic Stability

Genetic stability of the selected strains which produce a high proportion of alternan to dextran is determined. A strain is considered to be genetically stable for the purposes of this invention if the strain retains the phenotype after continuous growth for 60 generation cycles.

Selection of Strains That Produce a High Proportion of Alternan to Dextran

To obtain microorganism strains useful to serve as sources to obtain a polysaccharide product having a high proportion of alternan to dextran and/or an enzyme product having a high proportion of alternansucrase to dextransucrase, microorganism strains are screened by the rapid screening procedure described above. The screening procedure parameters identify strains that produce a high proportion of alternan to dextran, that is, microorganism strains that, when grown on a nutrient medium containing sucrose, produce alternan in an amount that is about 80% to 100% of total polysaccharide. The preferred strains produce at least about 88% or greater alternan. The percent alternan of total polysaccharide can be confirmed by the methods discussed above. The results of the radioassay can vary due to unknown factors. In the radioassay, pure alternan can show an experimental error of ±5%. Thus, it is suggested that percent alternan and percent alternansucrase be obtained from an average of at least three replicates. The strains obtained by screening are also checked for genetic stability.

Example 1, below, describes use of the screening procedure of the invention to screen approximately 5,280 mutagenized colonies prepared from strain *L. mesenteroides* NRRL B-1355. Mutant strain 515-F9 was identified as producing a high proportion of alternan to dextran. Analysis of the polysaccharide produced by the spent, cell-free culture fluid showed it to be alternan, with alternan purity estimated to be 88% ±8% of total polysaccharide as determined by radioassay. Genetic stability studies of the isolate showed it to be stable.

*L. mesenteroides* strain 515-F9 was deposited under terms of the Budapest Treaty on Sep. 2, 1993, in the Agricultural Research Culture Collection (NRRL) in Peoria Ill., and has been assigned the accession No. NRRL B-21138.

Uses of the Strains of the Invention

Fermentative Production of Alternan

Fermentative production of a product having a high proportion of alternan to dextran is accomplished by growing a microorganism strain having the properties described above, in any suitable nutrient medium containing sucrose as a carbon and fermentation substrate, until alternan accumulates, typically 2–3 days.

Typical nutrient media comprise sucrose and assimilable sources of nitrogen and inorganic salts. The sucrose concentration can be varied in a wide range, preferably 1 to 10% wt/vol. The fermentation is conducted under aerobic conditions or static culture, typically at 25°–28° C.

An alternan preparation can be isolated from the fermentation broth by removal of cells by standard methods such as by centrifugation or filtration. If desired, alternan is separated from the culture supernatant, for example, by treatment with an organic solvent in which alternan is insoluble, to precipitate the alternan. Typically, alternan is precipitated by the addition of ethanol in minimal concentrations, usually 50% or less final vol/vol. Precipitation concentrates the alternan product (dehydrates it) and purifies it from medium components. Other solvents useful for precipitation include methanol and isopropanol. The alternan product can be further purified by reprecipitation. Drying of the alternan product can be carried out by known procedures, for example, spray drying, oven-drying, or lyophilization.

Production of Alternansucrase

Strains selected by the method of the invention also have the characteristic that they produce a high proportion of the enzyme alternansucrase to the enzyme dextransucrase. Enzyme production is accomplished by cultivating the strain in a nutrient medium which contains the glucosyl donor substrate, sucrose, to induce enzyme synthesis. Growth is continued until alternansucrase is accumulated. Growth conditions for enzyme production are as described for alternan production, above. Maltose (an acceptor sugar) can be used to partially replace or supplement the sucrose growth substrate, thereby reducing the amount of polysaccharide produced. This has the advantage that lower polysaccharide levels result in lower viscosity and less association of polysaccharide with enzyme, which means easier handling of culture supernatants and/or purification of enzyme.

The fermentation broth can be used as crude enzyme preparation. Alternatively, a cell-free culture supernatant can be isolated from the fermentation broth by removal of cells such as by centrifugation or filtration. If desired, the enzyme in the supernatant can be concentrated by dialysis, ultrafiltration or other conventional means. The concentrate can be further purified by conventional means such as adsorption onto ion-exchange or hydrophobic interaction columns. Concentration and purification of sucrases are described by Cote and Robyt, supra.

Example 3, below, describes the fermentative production of alternansucrase using strain NRRL B-21138.

Enzymatic Production of Alternan

Alternan can be produced enzymatically, by the synthesis from sucrose using alternansucrase produced by strains obtained by the rapid screening procedure. Typically, the enzyme (crude preparation, cell-free culture supernatant, enzyme concentrate or pure enzyme) is added to a sucrose solution and incubated until alternan is formed. The alternan product is separated by precipitation with an organic solvent as described above. The product can be further purified and dried. Alternansucrase can also be used to synthesize alternan by immobilizing the enzyme onto a supporting material.

Example 4, below, describes the enzymatic production of alternansucrase using a crude enzyme solution prepared from strain NRRL B21138.

Use of alternansucrase to produce alternan has many advantages over production in growing cultures. One important advantage is that fructose is quantitatively produced as a valuable by product. Other advantages are that greater product uniformity can be obtained and synthetic conditions can be better controlled. Use of immobilized alternansucrase has the advantage that columns could be used for continuous production.

Use of Strains Selected by the Screening Procedure to Obtain Strains that Have Further Improvements Strains that produce a high proportion of alternan to dextran can also be used to develop secondary strain derivatives that have further improvements. This is carried out, for example, by preparing mutants of a strain selected by the screening procedure described above. The mutants are then screened. Strain 1138-G4 was isolated as a colonial morphology mutant of NRRL B21138, and subsequently characterized as a strain that overproduces alternansucrase.

Specifically, 1138-G4 produces approximately three-fold higher levels of alternansucrase than does NRRL B21138, while retaining the phenotype of producing a high proportion of alternan to dextran. Strain 1138-G4 produces an amount of alternan that is 92±4% of the total polysaccharide.

Example 5, below, describes the production of the secondary mutant, L. mesenteroides strain 1138-G4, from strain NRRL B-21138.

L. mesenteroides strain 1138-G4 was deposited under terms of the Budapest Treaty on Aug. 1, 1994, in the Agricultural Research Culture Collection (NRRL) in Peoria, Ill., and has been assigned the accession No. NRRL B-21297.

EXAMPLES

The following examples are intended only to further illustrate the invention and are not intended to limit the scope of the invention which is defined by the claims.

EXAMPLE 1

This example describes the rapid screening method of the invention to screen mutants generated from NRRL B-1355 to obtain a strain that produces a high proportion of alternan to dextran.

Mutagenesis. L. mesenteroides strain NRRL B-1355 was obtained from the ARS Culture Collection, Peoria, Ill. The strain was grown to midlog phase ($OD_{600}$ of 0.2 to 0.7) in the medium shown in Table A.

TABLE A

|  | % w/v |
|---|---|
| Sucrose | 2 |
| Polypeptone | 0.15 |
| Beef extract | 0.15 |
| Yeast extract | 0.15 |
| Tween 80 | 0.1 |
| Ammonium citrate | 0.2 |
| Sodium acetate | 0.5 |
| Magnesium sulfate heptahydrate | 0.01 |
| Manganese sulfate monohydrate | 0.005 |
| Potassium phosphate dibasic | 0.2 |
| pH adjusted to pH 6.5 | |

Liquid cultures were incubated at 28° C. with shaking at 100 rpm. Culture samples were diluted 1:100 into 10 mmol magnesium sulfate, and 5 ml volumes were placed in 100 mm sterile glass petri dishes and gently agitated. Mutagenesis was carried out using ultraviolet light. Cells were exposed to 300–350 $\mu W/cm^2$ radiation for 10 to 30 seconds. Aliquots (approximately 0.5 ml) were stored at –20° C. in 40% glycerol.

Samples showing approximately 99% mortality (usually exposed for 20 seconds) were further diluted in the 10 mmol magnesium sulfate and spread onto a solid medium containing sucrose (agar plate plus Table A medium) to produce isolated colonies. The plates were incubated at 28° C. in the dark for 1 to 2 days.

Mutant Screening. Isolated colonies were transferred onto fresh plates (agar plus Table A medium), denoted as master plates, in a grid pattern corresponding to 96-well microtiter dishes. The isolated colonies were grown overnight at 28° C. After growth, the master plates were used to inoculate liquid cultures (Table A medium) in sterile microtiter dishes (0.1 ml/well), which were grown without shaking for 2 days at 28° C.

Approximately 0.2 units of crude dextranase (1,6-α-D-glucan-6-glucanohydrolase, EC 3.2.1.11, from Penicillium sp. (D5884, Sigma Chemical Co., St. Louis, Mo.)) were added to each well, and the plates were mixed briefly and incubated for 2 hours at 37° C. Each plate included positive and negative control wells containing wild-type strain NRRL B-1355. The positive controls had dextranase added. Plates were tested for reducing sugar content, using dinitrosalicylic acid. Specifically, 0.1 ml of a solution consisting of 30% sodium potassium tartrate, 1.6% sodium hydroxide, and 1.0% dinitrosalicylic acid were added to the culture in each well. After mixing, plates were incubated at 80° C. for 15 to 30 minutes, until clear distinctions were apparent between the wells of positive and negative controls.

Putative mutant strains that produced a high proportion of alternan to dextran corresponded to the lighter wells similar to negative controls, while dextran-producing strains corresponded to the dark wells similar to the positive controls. Most of the colonies (approximately 99.6%) were indistinguishable from wild-type strain NRL B-1355 with respect to dextran production. A class of derivatives was also found that appeared to produce intermediate levels of dextran. The results are presented in Table 1.

Putative mutants that produced a high proportion of alternan to dextran were recovered from master plates, single colony purified twice, and retested for altered dextran production. Twenty isolates were found to retain their altered phenotype after purification using the liquid culture microtiter assay described above. These included 16 mutants that produced low levels of dextran and four that made intermediate levels of dextran. These mutants were streaked from primary (single-colony purified) stocks, and approximately 95 isolated colonies of each mutant were retested for mutant phenotypes. Ten of the 20 mutants showed less than 100% stability by this assay (designated "unstable" in Table 1).

Mutants stable by plate assay were cultured continuously by sequential transfer in liquid medium, for at least 60 generations. Samples were taken at regular intervals (approximately every eight generations) and tested for phenotype stability as described above. Two mutants (515-F9, low dextran; and 599-H11, intermediate dextran production) showed 100% stability after more than 60 generation cycles (designated "stable" in Table 1). The remaining mutants (designated "revertible" in Table 1) showed from 16 to 100% reversion after more than 60 generations.

Stable strain 515-F9 was cultured in volumes of up to 10 liters and confirmed to produce a high proportion of alternan to dextran in good yields.

Alternan produced in vitro from culture supernatants of 515-F9 was 88%±8% resistant to exhaustive digestion by dextranase when repeatedly cultured on the medium in Table A. This is discussed in detail in Example 2, below.

The test wells containing the strain were only slightly darker than negative control wells in the dinitrosalicyclic acid assay described above. The optical density of mutant strain 515-F9 wells was read at 540 nm. The negative control was used to zero the spectrophotometer. Mutant strain 515-F9 typically exhibited optical densities of about 0.1 to 0.3 OD unit higher than negative controls. The positive control wells typically exhibited optical densities 1.0 OD unit above those of negative control wells.

Reducing sugar concentrations of 515-F9 at 540 nm were estimated using a standard curve prepared from purified maltose in a concentration range of 10 mg/ml to 0.4 mg/ml. Negative control wells showed a reducing sugar background equivalent to approximately 2–4 mg/ml of maltose when read against a blank made up of 50 mM sodium acetate pH 5.0 buffer treated with the color reagent as described above. Positive control wells showed a reducing sugar response equivalent to approximately 4 mg/ml of maltose greater than negative controls (i.e., 6–8 mg/ml total maltose). Mutant strain 515-F9 wells showed a reducing sugar response equivalent to approximately 1–2 mg/ml maltose greater than negative controls (i.e., 3–5 mg/ml total maltose).

Alternan from mutant strain 515-F9 was also analyzed by the methylation procedure of Slodki et al., supra. Results, shown in Table 2, show that alternan from strain 515-F9 is identical to that from NRRL B-1355.

The taxonomic characteristics of L. mesenteroides strain 515-F9 are as follows: cells are spherical to lenticular, 0.5–0.7×0.7–1.2 micrometers, usually in pairs or short chains. Mucoid colonies (off-white to white) are formed on solid medium containing sucrose. The strain produces a high proportion of alternan to dextran.

Strain 515-F9 has the NRRL deposit number B-21138.

TABLE 1

Mutants of *Leuconostoc mesenteroides* strain NRRL B-1355

| Strain Number | Dextran production | Genetic Stability |
|---|---|---|
| 507-F8 | Low | Unstable[1] |
| 515-F9 | Low | Stable[2] |
| 566-E10 | Low | Unstable |
| 567-G3 | Low | Unstable |
| 568-D3 | Low | Unstable |
| 569-D6 | Low | Revertible[3] |
| 570-D7 | Low | Unstable |
| 570-E11 | Low | Unstable |
| 571-F4 | Low | Unstable |
| 571-F5 | Intermediate | Revertible |
| 572-B9 | Low | Revertible |
| 572-F9 | Low | Revertible |
| 574-E6 | Intermediate | Revertible |
| 599-H11 | Intermediate | Stable |
| 604-B12 | Low | Unstable |
| 606-D8 | Low | Unstable |
| 608-F8 | Low | Revertible |
| 616-A1 | Intermediate | Revertible |
| 618-D1 | Low | Revertible |
| 631-G4 | Low | Unstable |

[1] Greater than 1.0% revertants from primary isolates
[2] Less than 1.0% revertants after more than 60 generations
[3] Greater than 1.0% revertants after more than 60 generations

TABLE 2

Analysis of Alternan from *Leuconostoc mesenteroides* mutant 515F9
Mole Percentage of Methylated PAAN[1] Glucose Derivative

|  | 2,3,4,6-tetra-O—Me | 2,4,6-tri-O—Me | 2,3,4,-tri-O—Me | 2,4-di-O—Me |
|---|---|---|---|---|
| Purified Alternan | 10 | 35 | 45 | 10 |
| Alternan from 515F9 | 9 | 34 | 46 | 10 |

[1] per-O-acetylated aldononitrile

EXAMPLE 2

This example describes the determination of alternan purity in a mixture of alternan and dextran by radioassay. L. mesenteroides B-1355 (wild-type) was grown to stationary phase in a liquid medium. The bacterial cells were removed by centrifugation. The following were then mixed together:

0.60 ml of cell-free culture medium fluid 0.20 ml of 0.2M pH 5.4 sodium acetate buffer containing 0.1% sodium azide 0.20 ml of 0.3M $^{14}$C-labeled sucrose After standing at room temperature for three days, the reaction was mixed with an equal volume of ethanol. The precipitated polysaccharide was separated by centrifugation, redissolved in 1 ml of water, precipitated a second time, and redissolved in 1 ml of buffer. To this buffer was added 0.02 ml of endodextranase solution. At timed intervals (including t=0) 0.035 ml aliquots of this reaction mixture were removed and absorbed onto small squares (1.5 cm) of Whatman 3MM filter paper. At each time point, at least one square was simply dried, while at least one was first washed with methanol to removed non-polysaccharide material, then dried. Each was then counted by liquid scintillation to measure the amount of $^{14}$C on the paper square. At zero time (before any dextran hydrolysis had occurred), the unwashed square had 3000 cpm of radioactive material, and the washed had 3000 cpm. This means that essentially 100% of the radioactivity in the mixture was alcohol-precipitable, i.e., that only radioactive polysaccharide was present. By comparison, after the dextranase had been allowed to act for three hours, the unwashed square contained 3300 cpm and the alcohol-washed had only 1150 cpm. This means that of the total polysaccharide present initially, only 34% now remained as alcohol-precipitable material. After 24 hours, these numbers were unchanged, so it was evident that all of the polysaccharide that could be digested by dextranase had been digested within the first three hours. The conclusion is that the original bacterial culture fluid contained dextransucrase and alternansucrase in the ratio of 66:34 (i.e., 66% of the total glucan formed in a given time was dextran, and the remaining 34% was alternan).

Radioassays were carried out to determine the percent alternan of total polysaccharide from NRRL B-21138. Total glucansucrase activity from NRRL B-21138 was about half that of wild-type strain NRRL B-1355, similar to levels of alternansucrase purified from the wild type.

The mean percentage of alternan (of total polysaccharide) produced in vitro from culture supernatants of NRRL B-21138 was 88%, with a standard deviation of 8%. This value was obtained from 24 independent cultures (Table A medium). The mean percentage of alternan produced by the wild-type strain NRRL B-1355 was 69%, with a standard deviation of 8%. This value was from 10 independent cultures (Table A medium).

The effect of growth medium on the dextran levels produced may be significant. For example, we found that strain NRRL B-1355 (wild type) produced alternan in only 33% purity (% of total polysaccharide) when grown on Lawford's medium (Lawford, G. R., A. Kligerman, T. William, and H. G. Lawford, "Dextran Biosynthesis and Dextransucrase Production by Continuous Culture of *Leuconostoc mesenteroides*," Biotechnology and Bioengineering 21:1121–1131 (1979)), while strain NRRL B-21138 produced alternan in 94% purity.

EXAMPLE 3

This example describes the fermentative production of alternansucrase using strain NRRL B-21138. An active culture of strain B-21138 was inoculated into ten liters of liquid medium containing the following components: Polypeptone, 15 g; beef extract, 15 g; yeast extract, 15 g; sucrose, 200 g; maltose, 200 g; Tween 80, 5 g; ammonium citrate, 20 g; sodium acetate, 50 g, magnesium sulfate heptahydrate, 1 g; manganese sulfate, 0.5 g; monobasic potassium phosphate, 20 g; pH adjusted to 6.5 with hydrochloric acid or sodium hydroxide solution. The cultures were grown in six Fernbach flasks (approximately 1.67 L each), on a rotary shaker at approximately 120 rpm, at 28° C., for two days. At that time, the cells were removed by centrifugation. The cell-free culture fluid was concentrated approximately tenfold by ultrafiltration, using an ultrafiltration membrane with a molecular weight cutoff limit of no greater than 100,000. The concentrated cell-free culture fluid (approximately one liter) was then dialyzed against at least ten liters of 0.02M pH 5.4 sodium acetate buffer. This dialyzed material is referred to as the crude enzyme solution. It can be used as is, or further purified.

EXAMPLE 4

This example describes the enzymatic production of alternan using alternansucrase. One liter of the crude enzyme preparation described above is added to ten liters of an aqueous solution containing 1 kilogram of sucrose and an appropriate buffering agent (e.g., sodium acetate, pH 5.0–5.9) and a preservative (e.g., 0.1% sodium benzoate). After approximately 2–5 days at 20°–30° C., depending on the level of enzyme activity present, ten liters of ethanol are added to precipitate the alternan that has formed. The precipitate is collected by sedimentation, centrifugation, or filtration, and dried. Further purification of the product can be obtained by successive redissolution and precipitation steps, or by other means typically used in the purification of polysaccharides.

EXAMPLE 5

This example describes the production of a secondary mutant of NRRL B-21138 which overproduces alternansucrase. Specifically, isolated colonies representing mutagenized derivatives of NRRL B-21138 were produced as described in Example 1. These colonies were then replicated onto solid medium plates containing the medium in Table A, and also onto a solid medium similar to that in Table A except that maltose took the place of sucrose. Strain 1138-G4 was chosen as a colonial morphology mutant, i.e., the strain showed small and relatively non-mucoid colonies on solid medium plates containing sucrose. When 1138-G4 was characterized in liquid medium containing sucrose, it was found to produce elevated levels of alternansucrase, specifically about three-fold higher than strain NRRL B-21138. Furthermore, 1138-G4 retained the phenotype of NRRL B-21138 of producing a high proportion of alternan to dextran. The mean percentage of alternan (of total polysaccharide) of four independent cultures tested was 92% with a standard deviation of 4%.

*L. mesenteroides* strain 1138-G4 has been deposited under terms of the Budapest Treaty in the Agricultural Research Culture Collection (NRRL) in Peoria, Ill.

The taxonomic characteristics of *L. mesenteroides* strain 1138-G4 are as follows: cells are spherical to lenticular, 0.5–0.7×0.7–1.2 micrometers. Cells of strain 1138-G4 tend to be more spherical than those of *L. mesenteroides* strain NRRL B-21138, but still fall within the stated ranges. Cells usually appear in pairs or short chains, but strain 1138-G4 tends to form more short chains than does strain NRRL B-21138. Strain 1138-G4 forms off-white to white colonies on solid medium containing sucrose, but is far less mucoid than colonies of NRRL B-21138 on this medium, and may in fact be considered non-mucoid or only slightly mucoid.

It is understood that the foregoing detailed description is given merely by way of illustration and that modification and variations may be made therein without departing from the spirit and scope of the invention.

What is claimed is:

1. A rapid screening method to identify a bacterial test strain that produces a greater proportion of alternan to dextran, wherein said test strain is a strain of *Leuconostoc mesenteroides* or *L. dextranicum*, said method comprising in sequence:

(a) growing a test strain culture of a bacterial species known to produce alternan and dextran in a sucrose-containing liquid growth medium under conditions effective for production of polysaccharides;

(b) treating the liquid culture produced in step (a) with crude dextranase, wherein said crude dextranase contains enzymes which convert dextran and sucrose unused by the bacterial cells into reducing sugars and wherein bacterial cells have not been removed from said liquid culture produced in step (a);

(c) reacting the liquid culture produced in step (b), which contains bacterial cells, with a reagent that produces color in the presence of reducing sugars;

(d) measuring the optical density of the liquid test culture produced in step (c), from which bacterial cells have not been removed, at 540 nm and comparing the color produced by said test strain with the color produced by a negative control comprising a known alternan and dextran producing strain that has been grown and reacted with the color producing reagent under the same conditions as the test strain but that has not been treated with said crude dextranase; and (e) based on the comparison in step (d), identifying the test strain as a strain which produces a greater proportion of alternan to dextran if the optical density of the test strain liquid culture at 540 nm is no greater than about 0.3 optical density units higher than that of said negative control.

2. The method of claim 1 wherein said test strain is a mutant of *Leuconostoc mesenteroides* or *L. dextranicum*.

3. The method of claim 2 wherein said test strain is a mutant of *L. mesenteroides* strains NRRL B-1355, NRRL B-1498, or NRRL B-1501.

* * * * *